United States Patent
Gourley et al.

(10) Patent No.: US 6,416,783 B1
(45) Date of Patent: Jul. 9, 2002

(54) ASPARTIC AND MALIC ACID INHIBITION OF SS-GLUCURONIDASE

(75) Inventors: Glenn R. Gourley; Bill L. Kreamer, both of Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/641,597

(22) Filed: Aug. 18, 2000

Related U.S. Application Data

(60) Provisional application No. 60/150,158, filed on Aug. 20, 1999.

(51) Int. Cl.[7] .............................................. A61K 47/00
(52) U.S. Cl. ....................... 424/439; 424/400; 424/489; 514/893
(58) Field of Search ................................. 424/400, 439, 424/489; 514/893

(56) References Cited

U.S. PATENT DOCUMENTS

| | | |
|---|---|---|
| 4,753,926 A | 6/1988 | Lucas et al. |
| 5,068,184 A | 11/1991 | Knuth et al. |
| 5,212,235 A | 5/1993 | Nestaas et al. |

FOREIGN PATENT DOCUMENTS

| | | |
|---|---|---|
| EP | 059775 | 9/1982 |
| WO | WO/94/14458 | 7/1994 |

OTHER PUBLICATIONS

G. Gourley et al., The Effect Of Diet On Feces And Jaundice During The First 3 Weeks Of Life, 103 Gastroenterology 660–667 (1992).

G. Gourley et al., Inhibition of β–Glucuronidase By Casein Hydrolysate Formula, 25 J. Ped. Gast. & Nutr. 267–272 (1997).

G. Gourley, Bilirubin Metabolism And Kernicterus, 44 Advances In Pediatrics 173–229, Chapter 6 (1997).

G. Gourley et al., Neonatal Jaundice And Diet, 153 Arch. Ped. Adol. Med. 184–188 (1999) (presented at a May 2, 1997 meeting).

K. Kiyotani et al., Purification And Characterization Of β–Glucuronidase Inhibitor From *Mycobacterium tuberculosis*, 27 Microbiol. Immunol. 695–708 (1983).

D. Gray et al., Effect Of Aspartic Acid, Orotic Acid, And Glucose On Serum Bilirubin Concentrations In Infants Born Before Term, 46 Arch. Dis. Childhood 123–124 (1971).

I. Matsuda et al., Effects Of Aspartic Acid And Orotic Acid Upon Serum Bilirubin Level in Newborn Infants, 90 Tohoku J. Exp. Med. 133–136 (1966).

Amino Acid Breakdown Of Prior Art Formula (Nutramigen).

Pp. 6, 7, 9, 10, 896, 897, 1008 and 1009 of the 1989 publication Deutsche Forschungsanstalt Für Lebensmittelchemie (ED.): Food Compositions and Nutrition Tables, Wissenschaftliche Verlagsgesellschaft MBH Stuttgart XP002153764 (in English).

G. Eisenbrand et al., (ED.): "Römpp Lexikon Lembensmittelchemie" 1995, Georg Thieme Verlag, Stuttgart, New York XP002153765 p. 10.

S. Vaisman, et al., Pharmacologic Treatment of Neonatal Hyperbilirubinemia, Clinics in Perinatology, Symposium On Drug Therapy In The Neonate, vol. 2, No. 1, 27–57 (1975).

Partial crude translation of the summary section of A. Saito et al., Effect Of Aspartic Acid On Bilirubin Excretion, 27 Shohni–ka–Shinryo 124–128 (1964).

V. Hurgoiu, et al. Aspartofortul In Tratamentul Icterului La Prematuri*, 34 Pediatria 189–192 (1985) and partial crude translation thereof.

*Primary Examiner*—Thurman K. Page
*Assistant Examiner*—Claresse Evans
(74) *Attorney, Agent, or Firm*—Quarles & Brady LLP

(57) ABSTRACT

Disclosed herein are infant dietary supplements containing L-aspartic and/or L-malic acid. The supplements are designed to inhibit β-glucuronidase activity in breast feeding babies, and thereby suppress serum bilirubin levels and the incidence of neonate jaundice. In one form L-aspartic acid is mixed with human breast milk and fed to the neonate on the same schedule that breast feeding would otherwise normally occur. In another form the L-aspartic acid is delivered in an aqueous solution supplemented with sodium and potassium.

18 Claims, No Drawings

ASPARTIC AND MALIC ACID INHIBITION OF ß-GLUCURONIDASE

CROSS-REFERENCE TO RELATED APPLICATION

This application claims priority based on U.S. provisional application No. 60/150,158 filed Aug. 20, 1999.

STATEMENT REGARDING FEDERALLY SPONSORED SEARCH

This invention was made with United States government support awarded by the following agency: NIH Grant No. HD28619. The United States has certain rights in this invention.

BACKGROUND OF INVENTION

The present invention relates to formulations and methods useful in reducing serum bilirubin, and thus the incidence of infant jaundice, in breast feeding babies. More particularly, it relates to the use of L-aspartic acid and/or L-malic acid in formulas and supplements used in addition to breast milk.

Bilirubin is the red bile pigment formed during the catabolism of certain compounds such as hemoglobin. Human infants produce more bilirubin per unit of body weight than do adults because of greater red blood cell mass and shorter red blood cell life span. Bilirubin is poorly soluble in water and requires conjugation for excretion from the body.

Bilirubin is conjugated with glucuronic acid within the endoplasmic reticulum of the hepatocyte. Bilirubin conjugates in the intestine can act as a substrate for either bacterial or endogenous tissue β-glucuronidase. This enzyme hydrolyzes glucuronic acid from bilirubin glucuronide. The resulting unconjugated bilirubin produced is more rapidly absorbed from the intestine. This intestinal absorption of free bilirubin results in increased serum bilirubin levels in some neonates, which has been associated with infant jaundice.

More than thirty years ago aspartic acid was regarded as a possible therapy for neonatal jaundice in the belief that aspartic acid administration would increase uridine diphosphoglucuronic acid (UDPGA) concentration and resultant hepatic bilirubin conjugation. See S. Matsuda et al., 90 Tohoku J. Exp. Med. 133–136 (1966)(aspartic acid, 200 mg/day, was given to full-term newborn Japanese infants). The author of this article has indicated that the diet was formula rather than breast feeding.

See also A. Saito et al., 27 Shohni-ka-Shinryo 124 (1964) (serum bilirubin level decreased by administration of aspartic acid in some cases of hyperbilirubinemia); G. Kohno et al., 16 Shohni-ka-Rinsho 565–569 (1963) (a premature infant with neonatal hyperbilirubinemia had serum bilirubin level lowered by aspartic acid).

A subsequent Scottish double-blind study of pre-term formula-fed infants found no effect of aspartic acid on serum bilirubin concentrations when the aspartic acid was given for each of the first six days of life. See D. Gray et al., 46 Arch. Dis. Child. 123–124 (1971). This negative result marked the end of the period of investigations regarding the effects of aspartic acid on serum bilirubin levels.

It has been previously published that infants fed a certain type of casein hydrolysate formula (yet not certain other types of formula) had significantly lower levels of infant jaundice. It had been proposed that this is due to inhibition of β-glucuronidase by the formula. See G. Gourley, et al., 103 Gastroenterology 660–667 (1992); G. Gourley, et al., 25 J. Ped. Gast. & Nutr. 267–272 (1997); and G. Gourley, 44 Advances in Pediatrics 173–229, Chapter 6 (1997). The disclosure of these publications and of all other publications referred to herein are incorporated by reference as if fully set forth herein.

Pediatricians recommend breast feeding as the best way to feed neonates. However, notwithstanding the many benefits of breast feeding, it has been associated with increased levels of neonatal jaundice. Neonatal jaundice is mostly likely to occur during the first month (especially the first week) after a baby has been born. This is precisely the time that most mothers are attempting to breast feed. Thus, it is desirable to find a supplement that can be added to the breast milk itself which reduces the incidence of infant jaundice.

Further, even where a mother is willing to feed a formula (e.g. a casein hydrolysate based formula such as Nutramigen®) it is desirable to be able to optimize the ability of such formulas to reduce the incidence of neonate jaundice when initial signs of such jaundice appear.

Moreover, it is desirable to find ways to reduce the cost of adding supplements to the neonatal diet.

Thus, it can be seen that a need still exists for improved infant formulas and supplements.

BRIEF SUMMARY OF THE INVENTION

The inventors have discovered that L-aspartic acid and L-malic acid significantly inhibit β-glucuronidase, and that certain other components of conventional formula upregulate the production of β-glucuronidase. The supplementation of human breast milk with L-aspartic acid, but without other formula components that upregulate the production of β-glucuronidase, decreases the circulation of bilirubin in neonates, and hence is designed to reduce the frequency of jaundice in such neonates.

Important is the discovery of the mechanism of interaction of L-aspartic acid and L-malic acid with the body. The finding of β-glucuronidase inhibition enables the inventors to design and optimize a supplement for breast feeding neonates.

As such, the invention provides a method of administering a dietary supplement to a human infant that has at least in part been breast fed (preferably a newborn that is less than a month old). One administers to the infant a carrier mixed with L-aspartic acid and/or L-malic acid. The supplement does not contain any amino acids which stimulate β-glucuronidase activity under the "Standard Test" conditions specified below.

In preferred forms the infant is less than two days old at the time of the administration, the carrier is human breast milk or water, and the administration is oral feeding. Through the use of this method β-glucuronidase activity in the infant is inhibited and serum bilirubin levels can be reduced.

In another aspect the invention provides an infant formula containing breast milk and L-aspartic acid, L-malic acid, or mixtures thereof. The amino acid is at least in part exogenously supplied to the breast milk, in addition lo such L-aspartic acid and L-malic acid (if any) as the breast milk may naturally have.

In still another aspect the invention provides an infant formula containing a mix of at least seven amino acids, at least one of which is either L-aspartic acid or L-malic acid. The formula does not contain any amino acids which stimulate β-glucuronidase in the Standard Test described below.

In yet another form the invention provides an infant formula containing a plurality of amino acids derived via hydrolysis of casein, and L-aspartic acid and/or L-malic acid which is not derived from hydrolysis of casein (regardless of whether L-aspartic acid and/or L-malic acid from hydrolysis of casein is also present). Again, the formula does not contain any amino acids which stimulate β-glucuronidase in the Standard Test described below.

The invention can also provide a dietary supplement for an infant which is a fruit or vegetable juice mixed with L-aspartic acid and/or L-malic acid which is not derived from fruit or vegetable juice.

The advantages of the present invention therefore include providing:

(a) compounds of the above kind which can be used as supplements during breast-feeding;

(b) compounds of the above kind which help reduce serum bilirubin levels; and (c) methods for using such compounds.

These and still other advantages of the present invention will be apparent from the description which follows. The following description is merely of the preferred embodiments. The claims should therefore be looked to in order to understand the full scope of the invention.

DETAILED DESCRIPTION OF THE INVENTION

The Standard Test

We first developed a standard assay procedure (the "Standard Test"). We used human breast milk collected and pooled from a newborn nursery as the β-glucuronidase source. The samples were stored at −20° C. The milk was thawed and diluted 10× with 0.2 M sodium acetate/glacial acetic acid (NaAC) buffer pH 4.5 just prior to being used. A 4.0 mM stock solution of 4-methylumbelliferyl β-D-glucuronide (MUG, Sigma M-9130 lot#75H3777) was prepared in 0.2 M NaAC buffer pH 4.5.

Triplicate test and blank tubes contained a reaction mixture consisting of 50 μL diluted breast milk and 50 μL of an inhibitor solution diluted with 0.2 M NaAC buffer pH 4.5. Controls were prepared that contained only 50 μL diluted breast milk and 50 μL 0.2 M NaAC buffer pH 4.5. The assay was started by adding 25 μl of the MUG (4.0 mM, 0.800 mM final concentration) to the test sample to start the reaction. The final volume of the reaction was 125 μL. Both blank and test samples were vortexed and incubated at 37° C. for 1 hour (or for shorter times if indicated).

The reaction was quenched in both the test and blank samples with 3.0 ml of glycine-carbonate (320 mM: 200 mM) buffer pH 10.0. The blank samples had 25 μl of the MUG (4.0 mM, 0.800 mM final) added to them and all tubes were vortexed.

The resulting fluorescence was read using a Perkin Elmer LS5-B fluorescence spectrophotometer (360 nm excitation, 445 nm emission, autorange scale). The amount of 4-methylumbelliferone (4-MU) released by the β-glucuronidase was calculated using a 4-MU quadratic standard curve and the Mathplot software. The velocity was calculated as pmoles of 4-MU formed per hour per ml undiluted breast milk.

EXAMPLE 1

We diluted pooled breast milk 20× with 0.2 M NaAC buffer pH 4.5. We diluted 2.2% w/v solution of Amicase (Sigma Cat. #A2427—a mixture of free amino acids with virtually no unhydrolyzed peptides, only minimal inorganic components are present, total nitrogen ~12.8%, amino nitrogen ~9.8%) with buffer 5×. We then incubated 50 μl milk with 50 μl buffer and Amicase. We then added 25 μl MUG to start the reaction. We then quenched with Na-carbonate buffer pH 10.0 and read fluorescence at 360 nm ex 445 nm em. Autorange scale. The mixture of amino acids was compared to controls and Nutramigen® as follows:

TABLE 1

| D | Control | Nutramigen ® | Amicase |
|---|---------|--------------|---------|
| Activity | 295.7 | 71.7 | 209.8 |
| (pmole/ | 289.7 | 92.0 | 221.6 |
| tube/hr) | 306.2 | 105.7 | 213.9 |
|  | 299.6 | 97.5 | 216.7 |
|  | 304.2 | 86.8 | 209.3 |
|  | 302.1 | 96.8 | 211.2 |
| X̄ | 299.6 | 91.8 | 213.7 |
| SD | 6.1 | 11.7 | 4.7 |
| % | 100 | 30.6 | 71.3 |
| t |  | 38.7 | 27.3 |
| p | — | <10⁻⁷ | <10⁻⁷ |

Mixed amino acids did have some inhibitory activity on β-glucuronidase, but significantly less than that of Nutramigen® brand formula.

EXAMPLE 2

We then studied the effect of specific amino acid mixtures on β-glucuronidase activity. We diluted pooled breast milk 10× with 0.2 M NaAC buffer pH 4.5 and diluted 50×stock essential amino acid solution (Sigma Cat #M7020=L-arginine.HCl 6.32 g/L, L-cystine 1.2 g/L, L-histidine.HCl.H20 2.1 g/L, L-isoleucine 2.625 g/L, L-leucine 2.62 g/L, L-lysine.HCl 3.625 g/L, L-methionine 0.755 g/L, L-phenylalanine 1.65 g/L, L-threonine 2.38 g/L, L-tryptophane 0.51 g/L, L-tyrosine 1.8 g/L, L-valine 2.34 g/L).

We also used a non-essential AA solution=Sigma Cat #M7145=L-alanine HCl 0.89 g/L, L-asparagine.H20 1.50 g/L, L-aspartic acid 1.33 g/L, L-glutamic acid 1.47 g/L, glycine 0.75 g/L, L-proline 1.15 g/L, L-serine 1.05 g/L.

We 5×diluted 100×stock essential AA solution. We incubated 50 μl diluted milk with 50 μl buffer (control), or the essential AA solution, or the non-essential AA solution, or Nutramigen® RTU, added 25 μl MUG to start the reaction, quenched with Na-carbonate buffer, and read fluorescence (360 nm excitation: 445 nm emission). The results are as follows:

TABLE 2

| ID | Control (buffer) | Nutramigen ® (12.5 Dilution) | Minimum Essential Amino Acids | Minimum Non-Essential Amino Acids |
|----|------------------|-----------------------------|-------------------------------|-----------------------------------|
| Activity | 646.3 | 247.0 | 767.2 | 460.7 |
| (pmole/ | 685.4 | 242.7 | 764.0 | 459.2 |
| tube/hr) | 693.8 | 243.5 | 750.2 | 462.8 |
|  | 709.3 | 245.2 | 772.0 | 471.5 |
|  | 706.6 | 242.3 | 753.9 | 477.4 |
|  | 704.5 | 243.4 | 755.7 | 501.5 |
| X̄ | 691.0 | 244.0 | 760.5 | 472.2 |
| SD | 23.6 | 1.8 | 8.5 | 16.0 |
| % | 100.0 | 35.3 | 110.1 | 68.3 |

TABLE 2-continued

| ID | Control (buffer) | Nutramigen ® (12.5 Dilution) | Minimum Essential Amino Acids | Minimum Non-Essential Amino Acids |
|---|---|---|---|---|
| t | | 46.2 | −6.8 | 18.8 |
| p | — | <10⁻⁷ | 0.00005 | <10⁻⁷ |

The non-essential AA solution was inhibitory to β-glucuronidase, and the essential AA solution was somewhat stimulatory.

EXAMPLE 3

We then analyzed inhibitory effect of each of the seven amino acids in the non-essential amino acid mixture. We diluted pooled breast milk 10× with 0.2 M NaAC buffer pH 4.5, and diluted Nutramigen® RTU (N) and Nutramigen® lipid-free supernatant (LFS) 5 fold with 0.2 M NaAC buffer pH 4.5.

We prepared stock solutions of each of the non-essential amino acids L-alanine (Ala), L-asparagine (Asn), L-aspartic acid (Asp), L-glutamic acid (Glu), glycine (Gly), L-proline (Pro), and L-Serine (Ser). All solutions were at pH 4.5. The final concentration of each amino acid in the assay was the same as when the amino acids were analyzed as a mixture.

We then added 50 μl of diluted breast milk to 50 μl of stock solutions, added 25 μl MUG to start the reaction, quenched with Na-carbonate buffer pH 10.0, and read fluorescence at 360 nm ex 445 nm em. The results are as follows:

We concluded that the only one of these seven amino acids with significant β-glucuronidase inhibitory activity was L-aspartic acid. This inhibition was approximately the same as when these seven amino acids were tested for inhibitory activity together.

EXAMPLE 4

We then tested the main carbohydrates in casein for their effect. We diluted pooled breast milk 10× with 0.2 M NaAC buffer pH 4.5 and prepared stock solutions (25 mM, 2.5 mM and 0.25 mM) of the 3 major carbohydrate constituents of casein*: D(+)galactose (Sigma cat #G6404), N-acetyl-D-galactosamine (Sigma Cat #A2795), and N-acetylneuraminic acid (Sigma Cat #A0812).

We diluted Nutramigen® RTU (N) 5× with 0.2 M NaAC buffer pH 4.5, and added 50 μl of diluted breast milk to 50 μl of stock solutions, Nutramigen® or controls. Controls (C) received buffer in place of test stock solutions. We added 25 μl MUG to start the reaction, quenched with Na-carbonate buffer pH 10.0, and read fluorescence at 360 nm ex 445 nm em. The results are as follows for the following carbohydrates: N-acetyl-D-galactosamine (NAG) (0.1, 1, 10 mM) 98–100%; N-acetylneuraminic acid (0.1, 1, 10 mM) 99–100%; galactose (0.1, 1, 10 mM) 99%.

TABLE 3

| ID | Cont. | N | LFS | Ala | Asn | Asp | Glu | Gly | Pro | Ser |
|---|---|---|---|---|---|---|---|---|---|---|
| Conc. | | 12.5 × Dil | 12.5 × Dil | 35.6 μg/ml | 61.4 μg/ml | 53.2 μg/ml | 58.8 μg/ml | 30.0 μg/ml | 46.0 μg/ml | 42.2 μg/ml |
| Activity | 713.8 | 238.4 | 277.4 | 686.2 | 663.2 | 494.8 | 658.8 | 674.7 | 666.1 | 677.7 |
| (pmole/tube/hr) | 671.5 | 226.9 | 268.3 | 670.9 | 667.6 | 500.8 | 657.5 | 695.4 | 679.7 | 670.6 |
| | 662.6 | 236.3 | 264.4 | 656.0 | 646.7 | 493.9 | 663.7 | 686.5 | 662.9 | 659.2 |
| | 675.5 | | | | | | | | | |
| | 663.5 | | | | | | | | | |
| | 657.6 | | | | | | | | | |
| X̄ | 674.1 | 233.9 | 270.0 | 671.0 | 659.2 | 496.5 | 660.0 | 685.5 | 669.6 | 669.2 |
| SD | 20.5 | 6.2 | 6.7 | 15.1 | 11 | 3.7 | 3.3 | 10.4 | 8.9 | 9.3 |
| % | 100 | 34.7 | 40.1 | 99.5 | 97.8 | 73.7 | 97.9 | 101.7 | 99.3 | 99.3 |
| t | — | 35.3 | 32.3 | .2 | 1.2 | 14.4 | 1.1 | −0.9 | .4 | .4 |
| p | — | <10⁻⁷ | <10⁻⁷ | .8 | .3 | 0.000002 | .3 | .4 | .7 | .7 |

TABLE 4

| | C | N | D-gal | D-gal | D-gal | NAG | NAG | NAG | NAN | NAN | NAN |
|---|---|---|---|---|---|---|---|---|---|---|---|
| mM | | 12.5 X | 10 | 1 | 0.1 | 10 | 1 | 0.1 | 10 | 1 | 0.1 |
| | 821.3 | 301.3 | 806.6 | 825.6 | 816.8 | 835.1 | 805.6 | 811.8 | 897.8 | 829.9 | 806.4 |
| | 845.8 | 283.5 | 833.7 | 808.7 | 812.8 | 824.1 | 850.0 | 817.0 | 912.1 | 827.6 | 848.2 |
| | 825.9 | 287.6 | 821.3 | 802.5 | 830.9 | 824.3 | 809.3 | 813.4 | 907.2 | 803.9 | 810.9 |
| | 818.6 | | | | | | | | | | |
| | 826.1 | | | | | | | | | | |
| | 826.8 | | | | | | | | | | |
| X | 827.4 | 290.8 | 820.5 | 812.8 | 820.2 | 827.9 | 821.6 | 814.1 | 905.7 | 820.5 | 821.9 |
| Sd | 9.6 | 9.4 | 13.6 | 11.9 | 9.5 | 6.3 | 24.6 | 2.7 | 7.3 | 14.4 | 22.9 |
| % | 100 | 35.1 | 99.2 | 99.2 | 99.1 | 100.1 | 99.3 | 98.4 | 109.5 | 99.2 | 99.3 |

TABLE 4-continued

| | C | N | D-gal | D-gal | D-gal | NAG | NAG | NAG | NAN | NAN | NAN |
|---|---|---|---|---|---|---|---|---|---|---|---|
| t | 79.7 | | 0.9 | 2.1 | 1.1 | -.1 | 0.5 | 2.3 | -12.3 | 0.9 | 0.5 |
| p | $<10^{-7}$ | | 0.4 | 0.07 | 0.3 | 0.9 | 0.6 | .06 | 0.0000005 | 0.4 | 0.6 |

None of these tested carbohydrates show significant β-glucuronidase inhibition.

EXAMPLE 5

We then tested the effect of L- versus D-aspartic acid. We diluted pooled breast milk 10× with 0.2 M NaAC buffer pH 4.5 and diluted Nutramigen® RTU 5×. We then prepared stock solutions of the amino acids, added 50 μl of diluted breast milk to 50 μl of stock solutions, and added 25 μl MUG to start the reaction. We then quenched with Na-carbonate buffer pH 10.0 and read fluorescence at 360 nm ex 445 nm em. The stock solutions were 2.5× the final solution concentration. The results are as follows:

TABLE 5

| ID | Cont. | N | L-asp | L-asp | L-asp | L-asp | D-asp | D-asp | D-asp | D-asp |
|---|---|---|---|---|---|---|---|---|---|---|
| Conc. μm | | | 10,000 | 1,000 | 100 | 10 | 10,000 | 1,000 | 100 | 10 |
| Activity | 740.3 | 275.8 | 62.7 | 405.5 | 641.0 | 692.5 | 626.2 | 704.2 | 692.3 | 706.2 |
| (pmole/tube/hr) | 697.5 | 250.2 | 59.2 | 378.0 | 640.1 | 705.8 | 614.9 | 702.3 | 709.8 | 705.1 |
| | 709.6 | 256.3 | 58.6 | 349.1 | 628.0 | 683.2 | 602.9 | 691.2 | 682.1 | 691.7 |
| | 722.5 | | | | | | | | | |
| | 710.4 | | | | | | | | | |
| | 696.0 | | | | | | | | | |
| $\overline{X}$ | 712.7 | 260.8 | 60.2 | 377.5 | 636.4 | 693.9 | 614.7 | 699.2 | 694.8 | 701.0 |
| SD | 16.7 | 13.4 | 2.2 | 28.2 | 7.3 | 11.4 | 11.6 | 7 | 14 | 8.1 |
| % | 100 | 36.6 | 8.4 | 53.0 | 89.3 | 97.4 | 86.2 | 98.1 | 97.5 | 98.4 |
| t | | 40.5 | 65.3 | 23.0 | 7.4 | 1.7 | 9.0 | 1.3 | 1.6 | 1.1 |
| p | | .0000001 | .0000001 | .0000001 | .0002 | .1 | .00004 | .2 | .2 | .3 |

L-aspartic acid showed significant β-glucuronidase inhibitory activity at all concentrations great than 10 μM. Further β-glucuronidase inhibition by L-aspartic acid showed a dose response curve with maximum inhibition being at a level of only 8.4 percent of control at the highest concentration studied. D-aspartic acid was significantly inhibitory to β-glucuronidase only at the highest concentration, 10,000 μM. The inhibition of β-glucuronidase at this concentration was approximately equal to that of L-aspartic acid at 100 μM. Thus, L-aspartic acid was approximately 100 times more potent than D-aspartic acid in β-glucuronidase inhibition.

pH Experiments

We also ran experiments testing the effect of pH on the inhibition by L-aspartic acid of β-glucuronidase. Maximum inhibition was at about pH 5.

L-malic Acid

By similar experiments, we determined that L-malic acid also contributed to the inhibition of β-glucuronidase at similar concentrations to L-aspartic acid. We therefore believe that supplementing breast milk with L-malic acid would have similar effects.

Treatment Protocol

It is desirable to administer L-aspartic acid and/or L-malic acid to infants (particularly neonates suffering from infant jaundice). Preferably, this is done via oral administration of breast milk mixed with exogenously supplied L-aspartic acid and/or L-malic acid. Alternatively, other liquid carriers can be used such as water with 3:1 K:Na at concentrations of potassium and sodium similar to breast milk.

It is preferable to administer between 1 g and 5 g (preferably between 1 g and 3 g) of L-aspartic acid and/or L-malic acid per day to a neonate (e.g. for the first seven days of the baby's life). Typical unsupplemented breast feeding supplies about 400 mg of L-aspartic acid daily to a neonate. This can therefore be supplemented with about another 1100 mg. For example, each day the newborn can be supplied with six doses of 5 ml of supplement, with each supplement containing 180 mg of L-aspartic acid.

Alternatively, a standard casein hydrolysate infant formula (liquid or dry powder) can be supplemented with amounts of L-aspartic acid and/or L-malic acid that will deliver these amounts to the infant (taking into account such amounts of L-aspartic acid and/or L-malic acid as may already be in the hydrosylate and such levels of dilution as are recommended when normally using the formula).

The present invention is not to be limited to the specific examples described above. In this regard, there are other modifications that are meant to be within the scope of the invention. Thus, the claims should be looked to in order to judge the full scope of the invention.

Industrial Applicability

The present invention provides compounds useful for developing infant formulas and supplements, and methods of administering such compounds.

We claim:

1. A method of administering a dietary supplement to a human infant, comprising:
   providing to the human infant on a day breast milk; and
   on that same day administering to the human infant a dietary supplement consisting essentially of a carrier, and L-aspartic acid derived from other than human breast milk.

2. The method of claim 1, wherein the infant is less than two weeks old at the time of the administration.

3. The method of claim 1, wherein the carrier is human breast milk and the administration is by oral feeding.

4. The method of claim 1, wherein the infant has exhibited symptoms of jaundice prior to the administration.

5. The method of claim 1, whereby a serum bilirubin level in the infant is reduced.

6. An infant formula comprising:

human breast milk; and

L-aspartic acid that is obtained from other than human breast milk and exogenously supplied to the human breast milk.

7. A dietary supplement for an infant, comprising:

a carrier selected from the group consisting of a fruit and vegetable juice; and L-aspartic acid which is not derived from that carrier.

8. A method of administering a dietary supplement to a human infant, comprising:

providing to the human infant on a day breast milk; and on that same day administering to the human infant a dietary supplement comprising essentially of a carrier, and L-malic acid derived from other than human breast milk.

9. The method of claim 8, wherein the infant is less than two weeks old at the time of the administration.

10. The method of claim 8, wherein the carrier is human breast milk and the administration is by oral feeding.

11. The method of claim 8, wherein the infant has exhibited symptoms of jaundice prior to the administration.

12. The method of claim 8, whereby a serum bilirubin level in the infant is reduced.

13. An infant formula comprising:

human breast milk; and

L-malic acid that is obtained from other than human breast milk and exogenously supplied to the human breast milk.

14. An infant formula comprising:

a mix of at least seven amino acids, and L-malic acid;

wherein the formula does not contain any amino acids which stimulate β-glucuronidase activity under the Standard Test conditions specified herein.

15. An infant formula comprising:

a plurality of amino acids formed via hydrolysis of casein; and

L-malic acid which is not derived from hydrolysis of casein;

wherein the formula does not contain any amino acids which stimulate β-glucuronidase activity under the Standard Test conditions specified herein.

16. A dietary supplement for an infant, comprising:

a carrier selected from the group consisting of a fruit and vegetable juice; and L-malic acid which is not derived from that carrier.

17. A method of claim 1, wherein the supplement does not contain any amino acids which stimulate β-glucuronidase activity under the "Standard Test" conditions specified herein.

18. A method of claim 8, wherein the supplement does not contain any amino acids which stimulate β-glucuronidase activity under the "Standard Test" conditions specified herein.

* * * * *

UNITED STATES PATENT AND TRADEMARK OFFICE
CERTIFICATE OF CORRECTION

PATENT NO.   : 6,416,783 B1
DATED        : July 9, 2002
INVENTOR(S)  : Glenn R. Gourley and Bill L. Kreamer It is certified that error appears in the above-identified patent and that said Letters Patent is hereby corrected as shown below:

<u>Title page,</u>
Item [54], change "SS-GLUCURONIDASE" to -- β-GLUCURONIDASE --.

<u>Column 1,</u>
Line 11, change "SPONSORED SEARCH" to -- SPONSORED RESEARCH --.

<u>Column 2,</u>
Line 59, change "addition lo" to -- addition to --.

<u>Column 9,</u>
Line 19, change "comprising" to -- consisting --.

Please also replace Tables 3, 4 and 5 with the attached tables.

Signed and Sealed this

Seventh Day of January, 2003

JAMES E. ROGAN
*Director of the United States Patent and Trademark Office*

Table 3

| ID | Cont. | N | LFS | Ala | Asn | Asp | Glu | Gly | Pro | Ser |
|---|---|---|---|---|---|---|---|---|---|---|
| Conc. | | 12.5 x Dil | 12.5 x Dil | 35.6 µg/ml | 61.4 µg/ml | 53.2 µg/ml | 58.8 µg/ml | 30.0 µg/ml | 46.0 µg/ml | 42.2 µg/ml |
| Activity (pmole/ tube/hr) | 713.8 671.5 662.6 675.5 663.5 657.6 | 238.4 226.9 236.3 | 277.4 268.3 264.4 | 686.2 670.9 656.0 | 663.2 667.6 646.7 | 494.8 500.8 493.9 | 658.8 657.5 663.7 | 674.7 695.4 686.5 | 666.1 679.7 662.9 | 677.7 670.6 659.2 |
| $\bar{X}$ | 674.1 | 233.9 | 270.0 | 671.0 | 659.2 | 496.5 | 660.0 | 685.5 | 669.6 | 669.2 |
| SD | 20.5 | 6.2 | 6.7 | 15.1 | 11 | 3.7 | 3.3 | 10.4 | 8.9 | 9.3 |
| % | 100 | 34.7 | 40.1 | 99.5 | 97.8 | 73.7 | 97.9 | 101.7 | 99.3 | 99.3 |
| t | ------ | 35.3 | 32.3 | .2 | 1.2 | 14.4 | 1.1 | -0.9 | .4 | .4 |
| p | ------ | $< 10^{-7}$ | $< 10^{-7}$ | .8 | .3 | 0.000002 | .3 | .4 | .7 | .7 |

Table 4

| | C | N | D-gal | D-gal | D-gal | NAG | NAG | NAG | NAN | NAN | NAN |
|---|---|---|---|---|---|---|---|---|---|---|---|
| mM | | 12.5 X | 10 | 1 | 0.1 | 10 | 1 | 0.1 | 10 | 1 | 0.1 |
| | 821.3 845.8 825.9 818.6 826.1 826.8 | 301.3 283.5 287.6 | 806.6 833.7 821.3 | 825.6 808.7 802.5 | 816.8 812.8 830.9 | 835.1 824.1 824.3 | 805.6 850.0 809.3 | 811.8 817.0 813.4 | 897.8 912.1 907.2 | 829.9 827.6 803.9 | 806.4 848.2 810.9 |
| X | 827.4 | 290.8 | 820.5 | 812.2 | 820.2 | 827.9 | 821.6 | 814.1 | 905.7 | 820.5 | 821.9 |
| Sd | 9.6 | 9.4 | 13.6 | 11.8 | 9.5 | 6.3 | 24.6 | 2.7 | 7.3 | 14.4 | 22.9 |
| % | 100 | 35.1 | 99.2 | 98.2 | 99.1 | 100.1 | 99.3 | 98.4 | 109.5 | 99.2 | 99.3 |
| t | | 79.7 | 0.9 | 2.1 | 1.1 | -.1 | 0.5 | 2.3 | -12.3 | 0.9 | 0.5 |
| p | | $< 10^{-7}$ | 0.4 | 0.07 | 0.3 | 0.9 | 0.6 | .06 | 0.0000005 | 0.4 | 0.6 |

Table 5

| ID | Cont. | N | L-asp | L-asp | L-asp | L-asp | D-asp | D-asp | D-asp | D-asp |
|---|---|---|---|---|---|---|---|---|---|---|
| Conc. µM | | | 10,000 | 1,000 | 100 | 10 | 10,000 | 1,000 | 100 | 10 |
| Activity (pmole/ tube/hr) | 740.3 697.5 709.6 722.5 710.4 696.0 | 275.8 250.2 256.3 | 62.7 59.2 58.6 | 405.5 378.0 349.1 | 641.0 640.1 628.0 | 692.5 705.8 683.2 | 626.2 614.9 602.9 | 704.2 702.3 691.2 | 692.3 709.8 682.1 | 706.2 705.1 691.7 |
| $\bar{x}$ | 712.7 | 260.8 | 60.2 | 377.5 | 636.4 | 693.9 | 614.7 | 699.2 | 694.8 | 701.0 |
| SD | 16.7 | 13.4 | 2.2 | 28.2 | 7.3 | 11.4 | 11.6 | 7 | 14 | 8.1 |
| % | 100 | 36.6 | 8.4 | 53.0 | 89.3 | 97.4 | 86.2 | 98.1 | 97.5 | 98.4 |
| t | | 40.5 | 65.3 | 23.0 | 7.4 | 1.7 | 9.0 | 1.3 | 1.6 | 1.1 |
| p | | 0.0000001 | .0000001 | .0000001 | .0002 | .1 | .00004 | .2 | .2 | .3 |